United States Patent [19]

Siebenthaler

[11] Plant 4,654

[45] Feb. 24, 1981

[54] SUGAR MAPLE

[75] Inventor: John D. Siebenthaler, Dayton, Ohio

[73] Assignee: The Siebenthaler Company, Dayton, Ohio

[21] Appl. No.: 935,810

[22] Filed: Aug. 21, 1978

[51] Int. Cl.[3] ..... A01H 5/00

[52] U.S. Cl. ..... Plt./51

[58] Field of Search ..... Plt./51

*Primary Examiner*—Robert E. Bagwill
*Assistant Examiner*—James R. Feyrer
*Attorney, Agent, or Firm*—Biebel, French & Nauman

[57] ABSTRACT

A sugar maple of columnar form and exceedingly fast growth. The leaves have a less leathery appearance than other known columnar sugar maple trees which gives the tree an overall distinctive cleaner and healthier appearance. The leaves are less subject to scorching which adds to the healthy appearance of the tree particularly late in the season before the leaves change to their bright yellow coloration in the fall.

2 Drawing Figures

1

The present invention relates to a new and distinct variety of sugar maple tree known technically as *Acer saccharum*. I discovered my new variety as a seedling mutation of unknown parentage among a group of nursery plants of the *Acer saccharum* variety which were being grown in a cultivated area in a nursery in Dayton, Ohio.

My new variety of tree was asexually reproduced by budding in Dayton, Ohio. The new variety is characterized particularly by its distinctive columnar form, rapid growth rate, greater foliage for trunk size and less leathery in appearance of the leaves. In addition, the tree appears hardier than the species and exhibits less scorching late in the season to present a cleaner and healthier appearance than other known columnar sugar maples. The first seedling mutation resulting in the tree of the present invention is approximately twenty-six years old and is about 40 feet high and has the same spread from breast height to near the top of the tree. Younger trees of the present invention, for example, 4 year old trees, show over 20 percent more growth in height than other known columnar sugar maples of the same age, and exhibit their columnar form even at this early age.

A detailed comparison was made in applicant's nursery in Dayton, Ohio between the tree of the present invention and two other varieties which are commonly referred to in the trade as the Monumentaly Sentry and the Goldspire. The comparison clearly illustrated the distinctive appearance of the tree of the present invention over these two varieties in that it basically has the less leathery appearance of the leaves and healthier and cleaner look in the late fall due to less scorching of the leaves, as referred to above. The tree of the present invention also exhibits what could be called a smoother overall complexion than these other two varieties. The vigorous growth rate, mentioned above, was also evident from a comparison of the tree of the present invention with the Monumentaly Sentry and the Goldspire. For example, in comparison of four year old trees the tree of the present invention showed a height of 13 feet with the trunk diameter of 2⅛ inches, while the Goldspire was only 10 feet 6 inches high with a 2¼ inch diameter trunk. The Monumentaly Sentry is a much slower growing tree than the other two and at eight years was approximately the same height as the four year old Goldspire.

2

The tree exhibits some otherwise conventional and desirable characteristics of the species trees in that it maintains a green color throughout the summer turning to a brilliant yellow in autumn. In addition, this particular variety of the present invention has never exhibited any evidence of verticillium wilt which is a common problem in the area where the trees were grown nor has it exhibited any other common sugar maple maladies in its development history of approximately twenty-six years.

Figure 1:
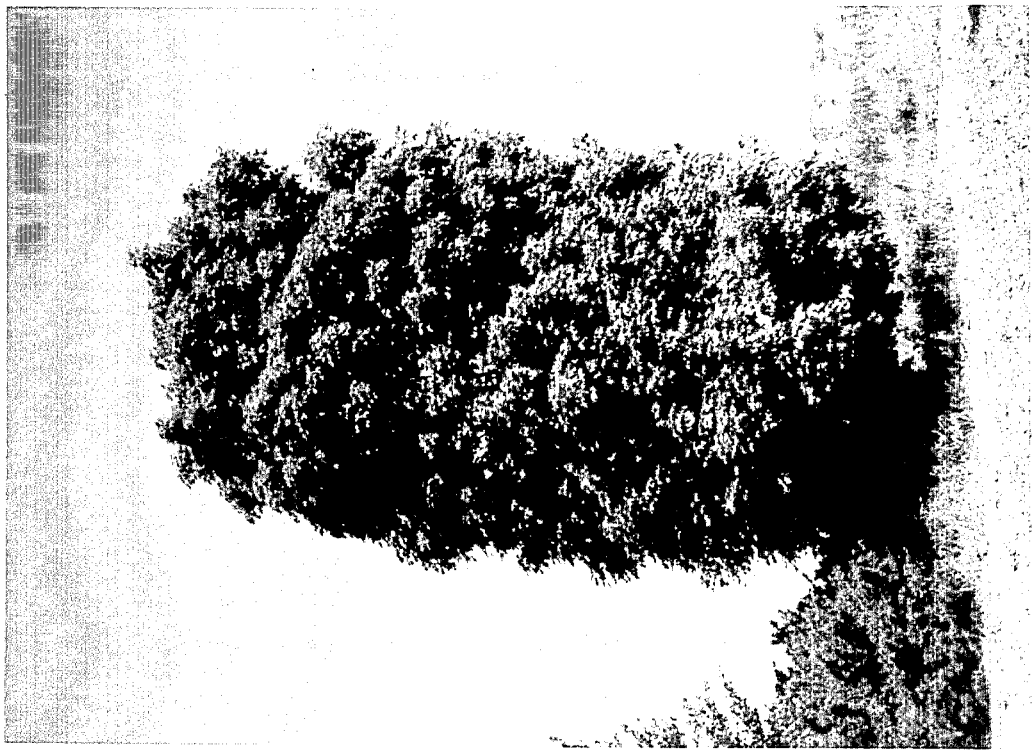
FIG. 1 is a color photograph of the tree of the present invention taken in the early summer of the year and showing the distinctive columnar appearance.
Figure 2:
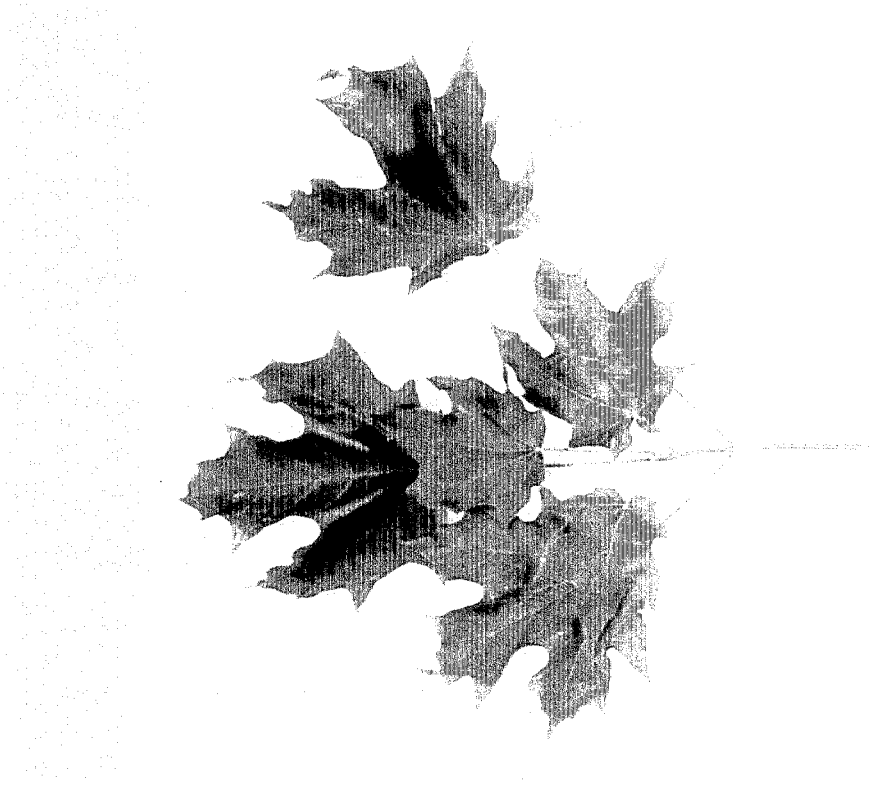
FIG. 2 is a color photograph of a branch of a tree of the present invention taken at the same time.
Figure 4:
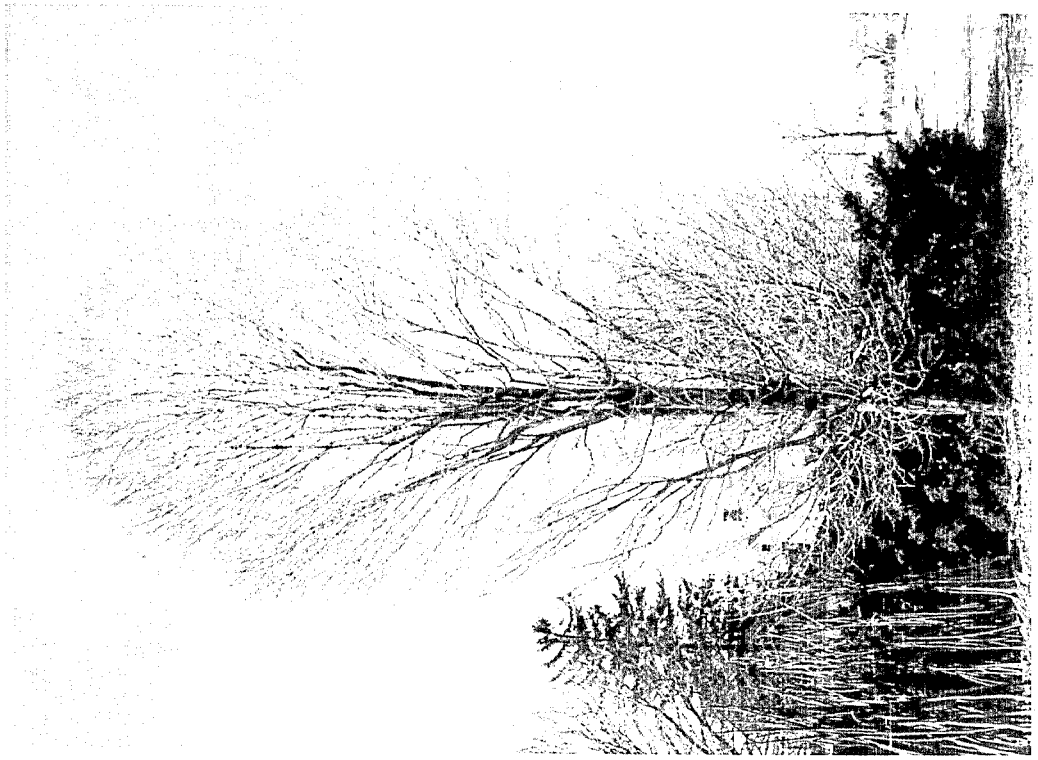
FIG. 4 is a black and white photograph of a defoliated tree of the present invention illustrating the columnar form of the branching structure.
Figure 3:
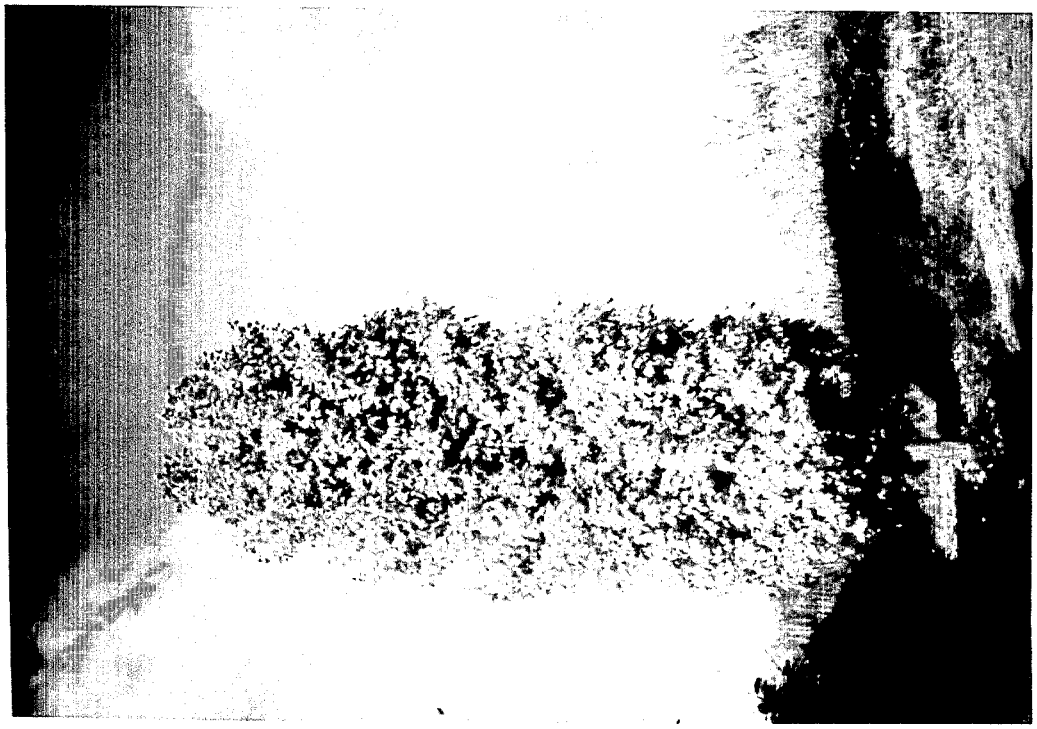
FIG. 3 is a color photograph of the tree of the present invention taken in the autumn to show the bright yellow coloration typical of the species.

The distinctive columnar shape referred to above and which is illustrated in FIG. 1, is maintained from a liner or young tree, through maturity. All of the budded reproduction from the initial seedling of this variety have maintained this columnar form.

The following is a detailed description of my new variety of *Acer saccharum*, with color terminology in accordance with the "Royal Horticultural Society Colour Chart", published by The Royal Horticultural Society of London. It is pointed out, however, that the coloration of leaves as indicated below are only approximate because the color variation is considerable as the leaves age during a season. In addition, the size of the leaves vary from tree to tree and in the same tree and depend to some extent on the weather during the growing season.

Parentage: A seedling mutation of unknown parentage.

Propagation: Holds to distinguishing characteristics through succeeding propagation by budding.

Locality where grown and observed: Dayton, Ohio.

Tree: Upright, columnar and healthy; vigorous growth rate observed to be over 20 percent greater than other known columnar sugar maples; branches turn upward and are fairly symmetrical about the trunk producing a uniform columnar appearance; the head is broader than other known columnar sugar maples thus maintaining the columnar appearances at the top as well; bark is smooth as is common of the species.

Foliage: Leaves are 3 to 5 inches wide across the widest points perpendicular to the petiole and are lobed cordate, 3 to 6 inches long from the base of the vanes at the petiole to the tip; the petiole is generally longer and more delicate than other known columnar sugar maples and range in length generally 5½ to 7½ inches; the leaves are less leathery in appearance than the species, giving the tree an overall clearly distinctive appearance from other columnar sugar maples; the leaves have narrow and deep sinuses, lobes are acuminate and sparingly dentate; usually glaucous on top and glabrous beneath; no seeding has been observed.

Color: Scheels green 860/1 through the summer and turning in autumn to yellow achre 07/1 with slight blends of Indian orange 713/1.

I claim:

1. A new and distinct variety of *Acer saccharum* substantially as herein shown and described, characterized particularly by its columnar shape vigorous growth faster than other known columnar sugar maples, less leathery appearance of the leaves and cleaner and healthier appearance late in the season due to less scorching of the leaves.

* * * * *